(12) United States Patent
Bossi et al.

(10) Patent No.: US 8,342,017 B1
(45) Date of Patent: Jan. 1, 2013

(54) METHODS FOR FABRICATING FIBER-REINFORCED PLASTIC TEST SPECIMEN ASSEMBLIES HAVING WEAK ADHESIVE BONDS

(75) Inventors: Richard Henry Bossi, Renton, WA (US); Marc J. Piehl, Renton, WA (US); Douglas Allen Frisch, Renton, WA (US); Kay Y. Blohowiak, Issaquah, WA (US); William B. Grace, Seattle, WA (US); Peter J. Van Voast, Seattle, WA (US)

(73) Assignee: The Boeing Company, Chicago, IL (US)

( * ) Notice: Subject to any disclaimer, the term of this patent is extended or adjusted under 35 U.S.C. 154(b) by 254 days.

(21) Appl. No.: 12/908,032

(22) Filed: Oct. 20, 2010

(51) Int. Cl.
*G01N 19/04* (2006.01)

(52) U.S. Cl. ..................................... 73/150 A

(58) Field of Classification Search .................. None
See application file for complete search history.

(56) References Cited

U.S. PATENT DOCUMENTS

| | | | | |
|---|---|---|---|---|
| 3,962,498 A * | 6/1976 | Owston | | 427/322 |
| 6,551,407 B2 | 4/2003 | Drzal et al. | | |
| 6,565,927 B1 | 5/2003 | Drzal et al. | | |
| 6,622,568 B2 | 9/2003 | Nelson et al. | | |
| 6,692,595 B2 * | 2/2004 | Wheatley et al. | | 156/71 |
| 6,848,321 B2 * | 2/2005 | Bossi et al. | | 73/842 |
| RE39,839 E * | 9/2007 | Wheatley et al. | | 156/71 |
| 7,507,312 B2 | 3/2009 | Bossi et al. | | |
| 7,509,876 B1 | 3/2009 | Sokol et al. | | |
| 2007/0149080 A1 * | 6/2007 | Asahara et al. | | 442/239 |
| 2010/0181017 A1 * | 7/2010 | Shinoda et al. | | 156/242 |
| 2010/0285265 A1 * | 11/2010 | Shinoda et al. | | 428/80 |

OTHER PUBLICATIONS

R.G. Dillingham, S. Conyne-Rapin, F. J. Boerio, R. H. Bossi and R. Crane, "Surface Preparation of Composite Materials for Adhesive Bonding," Proc. 26th Annual Meeting of the Adhesion Society, Myrtle Beach, SC, Feb. 2003.
R. H. Bossi, K. R. Housen and W. B. Shepherd, "Application of Stress Waves to Bond Inspection," SAMPE 2004, Long Beach, CA., May 16-20, 2004.
Richard Bossi, Robert Carlsen, F. James Boerio and Giles Dillingham, "Composite Surface Preparation QA for Bonding," 50th International SAMPE Symposium, Long Beach, CA, May 1-5, 2005.
R. Bossi, K. Housen, C. Walters and D. Sokol, "Laser Bond Testing," Materials Evaluation, vol. 67, No. 7, Jul. 2009, pp. 819-827.
P. Van Voast, P. Shelley, R. Blakley, C. Smith, M. Jones, A. Tracey, B. Flinn, G. Dillingham and B. Oakley, "Effect of Varying Levels of Peel Ply Contamination on Adhesion Threshold," SAMPE 2010, May 17-20, Seattle, WA.

(Continued)

*Primary Examiner* — Andre Allen
(74) *Attorney, Agent, or Firm* — Ostrager Chong Flaherty & Broitman P.C.

(57) ABSTRACT

A method for repeatably fabricating a test specimen assembly comprising a pair of fiber-reinforced plastic (FRP) test specimens adhesively bonded together, the bonded joint having respective areas of substantially different, but consistent variable adhesive bond strengths suitable as a calibration standard. The method comprises fabricating a first FRP test specimen having a bonding surface with first and second areas that have substantially different bonded joint performance-governing characteristics and then using adhesive to bond the bonding surface of the first FRP test specimen to the bonding surface of a second FRP test specimen. The different bonded joint performance-governing characteristics are achieved by treating first and second areas of the surface of the first FRP test specimen using different respective surface preparation techniques.

20 Claims, 9 Drawing Sheets

OTHER PUBLICATIONS

Kay Y. Blohowiak, Peter J. Van Voast, Paul H. Shelley and Jacob W. Grob, "Nonchemical Surface Treatments Using Energetic Systems for Structural Adhesive Bonding," SAMPE 2010, May 17-20, Seattle, WA.

P. Van Voast, P. Shelley, R. Blakley, C. Smith, M. Jones, A. Tracey, B. Flinn, G. Dillingham and B. Oakley, "Effect of Varying Levels of Peel Ply Contamination on Adhesion Threshold," SAMPE 2010, May 17-20, Seattle, WA [PowerPoint Presentation].

Brian D. Flinn, "Improving Adhesive Bonding of Composites Through Surface Characterization," The Joint Advanced Materials and Structures Center of Excellence [PowerPoint Presentation].

Brian D. Flinn and Molly Phariss, "Improving Adhesive Bonding of Composites Through Surface Characterization," The Joint Advanced Materials and Structures Center of Excellence [PowerPoint Presentation].

Richard Bossi, Kevin Housen and Craig Walters, "Bond Strength Measurement Using a Laser Bond Inspection Device," SAMPE 2004, May 16-20, Long Beach, CA.

Brian D. Flinn and Molly Phariss, "The Effect of Peel-Ply Surface Preparation Variables on Bond Quality," DOT/FAA/AR-06/28, Final Report, Aug. 2006.

* cited by examiner

METHODS FOR FABRICATING FIBER-REINFORCED PLASTIC TEST SPECIMEN ASSEMBLIES HAVING WEAK ADHESIVE BONDS

BACKGROUND

This invention generally relates to methods for assembling a fiber-reinforced plastic (FRP) structure by adhesive bonding of respective FRP subcomponents. In particular, the invention relates to methods for ensuring that the adhesive bond between two FRP subcomponents has adequate strength.

Adhesive bonding is an important joining method for aerospace structures. Strong, durable bonded joints are created by proper selection of the materials (adherends and adhesive), processing, assembly and cure. The certification of the bond requires that the strength be validated. Methods are needed to validate that bond strength measurement techniques are in calibration.

Validation of the bond strength involves a combination of process control validation and final bond quality validation. The development and implementation of bond quality validation, that returns an estimate of the bond strength, requires standards (also referred to herein as "test specimen assemblies") containing controlled levels of bond strength for calibration. A critical issue is that the weak bond standards be constructed without physical features or characteristics that can be detected by standard nondestructive inspection (NDI) methods such as ultrasound, infrared, shearography or x-ray. These standard NDI methods are performed on bonded structure to validate assembly issues and find unbonded regions. However, they are not necessarily capable of detecting weak bonds. Alternative inspection approaches for weak bond detection are needed and must be applicable to bonds that would be acceptable by the standard NDI processes. The standard needs to be constructed in a repeatable manner so that, as required, additional standards can be made. Further, the standard needs to possess variable strength bonds from weak to full strength. Finally the standard should be adaptable to the adherend thickness used in the actual construction of the adhesive joint of interest.

Such a standard would be useful for testing NDI methods of any type to determine whether the method is possibly sensitive to a weak bond interface. For the inspection methods that test for strength using loading of the bond in the testing, the standard will be mechanically failed as part of the testing and will therefore need to be replaced frequently Weak bonds have been found in practice due to variation in the manufacturing technique. In particular, incorrect material, surface preparation and contamination are key variables that can create weak bonds that are not detectable by NDI methods. Other processes, such as incorrect assembly or curing can result in features or material change effects that can be detected by NDI techniques. The creation of useful weak bond standards therefore resides in finding a controlled manner of degrading the interface for adhesion without creating features that are detectable by standard NDI methods. Thus the weak bond standards should represent the case of bonds that pass standard ultrasonic inspection but do not have full strength. It would desirable to have a range of strengths such as one third, two thirds and full strength or 25, 50, 75 and 100% of full strength in the standards for calibration of the bond strength test method.

Weak bonds have been created in the past by adding chemical mixtures, distributing contaminates or disrupting a surface. Known methods of creating weak bonds can be difficult to repeat or will have features that can be detected by standard NDI methods. For example, poly film and aged adhesive methods can create weak interfaces, but the interface degradation is detectable by standard NDI methods. Variable grit blast methods have also been successful in creating variable strength bonds. The surface condition however is such that it is also possible with detailed inspections to detect the surface feature with standard NDI methods.

The problem to be solved was that, if a system were developed that could detect weak bonds, how could the system be calibrated and how would one know that it was operating correctly to detect a weak bond if one should exist.

BRIEF SUMMARY

The present invention solves the aforementioned problem by providing manufactured standards, i.e., test specimen assemblies, having variable bond strengths which can be repeatably duplicated for validating that a bond strength measurement system can in fact correctly detect a weak bond. Standards made in accordance with the methods disclosed herein can be used to validate that the certification method on a bonding process can in fact detect a weak (less than full strength) bond. A consistent bond is created that has variable strength but lacks features detectable by conventional NDI methods.

The invention encompasses various methods for repeatable surface preparation that can be used to manufacture weak bond standards having weak bond strengths not detectable by standard NDI techniques. The repeatable surface preparation techniques disclosed herein vary the activation of one of the surfaces to be bonded. The methods of manufacture disclosed herein can be used in any thickness of bond configuration based on the FRP thickness that it is applied to. Bonds created by these methods are indistinguishable in standard NDI examinations.

One aspect of the invention is a method for fabricating a test specimen assembly comprising the following steps: (a) fabricating a first FRP test specimen having a bonding surface, wherein a first area of the bonding surface of the first FRP test specimen has a first bonded joint performance-governing characteristic, while a second area of the bonding surface, not overlapping with the first area, of the first FRP test specimen has a second bonded joint performance-governing characteristic different than the first bonded joint performance-governing characteristic; (b) fabricating a second FRP test specimen having a bonding surface; (c) placing the bonding surface of the first FRP test specimen in overlapping relationship with the bonding surface of the second FRP test specimen with adhesive therebetween, the adhesive being in contact with the first and second areas of the bonding surface of the first FRP test specimen and with the bonding surface of the second FRP test specimen; and (d) curing the adhesive to bond the first and second FRP test specimens together.

In accordance with some embodiments, the manufactured standard has variable bond strengths due to the use of different peel plies in the assembly. The method of manufacture uses a consistent product in the form of peel ply materials that are applied to the FRPs during the fabrication. Each peel ply type will result in a consistent surface type for bonding that will have different bond strength when assembled with the prescribed adhesive method.

In accordance with one specific embodiment, the standard is constructed using three different peel plies in each of three regions of one of the adherends to be adhesive bonded. When the other adherend is assembled to the adherend that was prepared with three different peel plies after removal of the latter, the resulting adhesive bond will have zones of three different bond strengths. The adhesive bond strengths will be consistent whenever the process is repeated because of the consistency of the peel ply materials.

In accordance with other embodiments, a commercially available peel ply material can be soaked for a controlled time in a concentrated bath containing release agent materials. By controlling the concentration and time, variable levels of peel ply contamination can be achieved.

In accordance with one specific embodiment, the standard is constructed using three peel plies in each of three regions of one of the adherends to be adhesive bonded, two of the peel plies having different levels of contamination by a release agent material and the third peel ply being uncontaminated. When the other adherend is assembled to the adherend that was prepared with three different peel plies, the resulting adhesive bond will have zones of three different bond strengths.

In accordance with other embodiments, the manufactured standard has variable bond strengths due to different surface treatments using energetic systems (such as systems for directing a plasma jet or a laser beam over a surface to be treated). In accordance with one such embodiment, a plasma jet is raster scanned over first and second areas of a first FRP test specimen under first and second sets of plasma conditions respectively. In accordance with another such embodiment, a laser beam is raster scanned over first and second areas of a first FRP test specimen under first and second sets of laser conditions respectively. When the differentially surface-treated first FRP test specimen and a second FRP test specimen are adhesively bonded, the result will be adhesive bonds of different strengths in the first and second areas.

Other aspects of the invention are disclosed and claimed below.

BRIEF DESCRIPTION OF THE DRAWINGS

Reference will hereinafter be made to the drawings in which similar elements in different drawings bear the same reference numerals.

DETAILED DESCRIPTION

The integrity of an adhesive bond between two FRP laminates depends on strong chemical bonding and mechanical factors. Surface preparation can remove contamination and create a chemically active surface. Sanding, grit blasting, peel-ply removal and energetic surface preparation are known methods for preparing a FRP surface for adhesive bonding with another FRP surface.

The characteristics of the adherend are critical to the integrity of an adhesive bond. Because adhesion is a function of the chemical and physical nature of the surface, the properties of that surface will often govern the performance of a bonded joint. Surface characteristics that affect performance include: (1) surface roughness; (2) surface energy; (3) cleanliness/removal of contamination; and (4) chemical activity/functionality.

Various methods for repeatable surface preparation that can be used to manufacture weak bond standards having weak bond strengths not detectable by standard NDI techniques will now be described. The repeatable surface preparation techniques disclosed herein vary the activation of one of the surfaces to be bonded. The methods of manufacture disclosed herein can be used in any thickness of bond configuration based on the FRP thickness that it is applied to. Bonds created by these methods are indistinguishable in standard NDI examinations.

More specifically, some of the methods disclosed herein for fabricating a test specimen assembly comprise preparing the bonding surface of a first FRP adherend so that different areas on that bonding surface have different bonded joint performance-governing characteristics. A second FRP adherend having a uniform bonded joint performance-governing characteristic is then adhesively bonded to the first adherend, resulting in a test specimen assembly having a bonded joint with respective areas that have different adhesive bond strengths. This test specimen assembly is suitable for use as a standard when validating that a bond strength measurement system can in fact correctly detect a weak bond.

Figure 1:
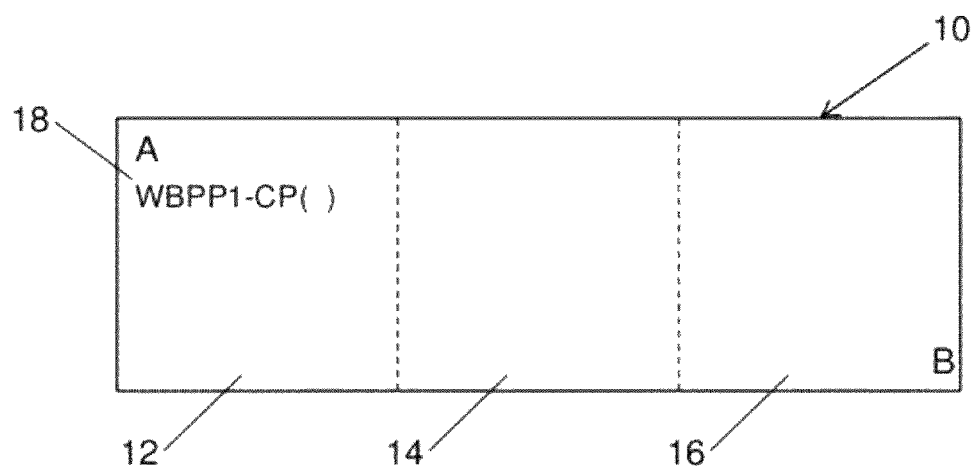
FIG. 1 is a drawing showing a plan view of a weak adhesive bond test specimen assembly in accordance with various embodiments of the invention.

The structure of an exemplary FRP test specimen assembly or standard 10 is shown in FIG. 1. In this example, the bonded joint of the FRP standard 10 has three areas 12, 14 and 16 in which the respective adhesive bond strengths differ from each other to a substantial degree. Each standard 10 is provided with an identifying label 18, e.g., WBPP1-CP1 through WBPP1-CP12 in the case wherein a precursor test specimen assembly was sectioned into 12 coupons or standards. The designations A and B seen in FIG. 1 indicate the orientation of the standard.

Figure 2:
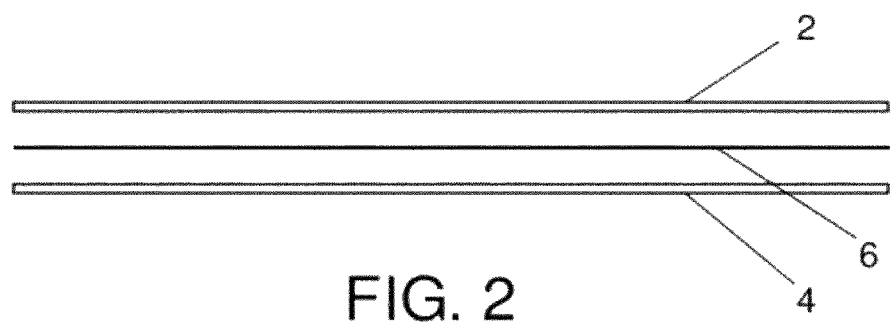
FIG. 2 is a drawing showing an exploded side view of the weak adhesive bond test specimen assembly depicted in FIG. 1.

As shown in FIG. 2, each test standard disclosed herein comprises first and second FRP laminates 2 and 4 that will be bonded together by adhesive 6. These components are depicted in the exploded view of FIG. 2 as being separated, but it should be appreciated that in the final assembled state the laminates 2 and 4 will both be in contact with and bonded by the cured adhesive 6 therebetween.

In accordance with the embodiments disclosed hereinafter, respective areas of a bonding surface of a FRP adherend (corresponding to the areas 12, 14 and 16 depicted in FIG. 1) may be treated using peel plies, plasma jets or laser beams.

Peel Ply-Based Adhesion for FRP-to-FRP Bonds

In accordance with some embodiments, the manufactured standard has variable bond strengths due to the use of different peel plies in the assembly. The method of manufacture uses a consistent product in the form of peel ply materials that are applied to the FRPs during the fabrication. Each peel ply type will result in a consistent surface type for bonding that will have different bond strength when assembled with the prescribed adhesive method.

A peel ply is a woven fabric that may be applied as the first or last layer on a FRP prepreg assembly before the part is cured. During cure, the epoxy in the first FRP part becomes viscous and flows into gaps in the peel ply. The peel ply is removed from the surface of the first FRP part immediately before the latter is adhesively bonded to a second FRP part. Because the peel ply does not bond to the first FRP part, it can be readily peeled off, leaving a surface texture on the first FRP part which is suitable for adhesive bonding to the surface of the second FRP part. The removal of the peel ply leaves a roughened surface on the first FRP part that does not require further processing (e.g., sanding or grit blasting) before laminating or bonding to the second FRP part.

Peel ply is used in the fabrication of FRP parts to protect a surface during handling and as a surface preparation method for a future bonding process. The peel ply comes in a variety of types from each manufacturer. Peel ply is normally a fabric layer that may be made from materials such as fiberglass, Kevlar, nylon or polyester. The peel ply is placed as the first ply on a tool surface and then the FRP layup is assembled. Following cure, the FRP part will be transported for a further assembly operation. At the time of the further assembly, the peel ply layer will be removed leaving a fresh surface for bonding. The peel ply removal is performed just prior to the bonding operation. The surface that is available for bonding will have a chemistry and texture that is a function of the peel ply used. Based on the peel ply type and the adhesive, variable strength will be found in the adhesive bond.

During the evaluation of adhesive bonding surface preparation methods, several types of peel ply have been investigated. The results of that study found that the peel ply could be used to develop controlled bond strength in a consistent, repeatable manner. Table 1 in the Appendix lists the peel ply types (manufactured by Precision Fabrics Group Inc.) that have been found to represent variable peel ply strength when used with AF 555 adhesive and BMS Toray FL96736-37K Type 40, Class 2, Style 6K-70-PW, Form 1 FRP material (manufactured by Toray Industries Inc.) using 350° F. curing.

Technical descriptions of the selected peel ply materials (all manufactured by Precision Fabrics Group) are as follows:

Polyester Peel Ply Fabric:
Code 60001
Style: 56009
Fiber: 100% polyester
Finish: Fin 060 NAT, Scoured and Heat Set
Finished Count (ASTM D 3775): 70 ends/inch Warp; 50 picks/inch FILL Nylon Peel Ply Fabric:
Code 51789
Style: 52006
Fiber: 100% nylon 6, 6
Finish: Fin 060 NAT, Scoured and Heat Set
Finished Count (ASTM D 3775): 160 ends/inch Warp; 103 picks/inch FILL Nylon Peel Ply Fabric with Silicon Release Additive:
Code 51789
Style: 52006
Fiber: 100% nylon 6, 6
Finish: Fin 061 SRB, Super release Blue—an inert, heat-stabilized cross-linked polymer finish
Finished Count (ASTM D 3775): 160 ends/inch Warp; 103 picks/inch FILL As used herein, the term "AF 555 adhesive" refers to 3M™ Scotch-Weld™ Structural Adhesive Film AF 555. AF 555 adhesive is a 350° F. curing film designed for metal and FRP bonding in conjunction with honeycomb (sandwich construction) or in a laminate structure. This film can also be utilized for FRP surfacing. AF 555 film can be co-cured, co-bonded with FRP pre-pregs, or used to bond cured FRP.

FRP-to-FRP Peel Ply-Based Bond Standard

In accordance with one specific embodiment, the standard is constructed using three different peel plies in each of three regions of one of the adherends to be adhesively bonded. When the other adherend is assembled to the adherend that was prepared with three different peel plies after removal of the latter, the resulting adhesive bond will have zones of three different bond strengths. The adhesive bond strengths will be consistent whenever the process is repeated because of the consistency of the peel ply materials.

The aforementioned specific embodiment used nylon 6,6 SRB, nylon 6,6 and polyester peel plies (as described in Table 1) applied to one surface of a first laminate made of Toray FL96736-37K Type 40, Class 2, Style 6K-70-PW, Form 1 FRP material, while a single polyester peel ply was applied to one surface of a second laminate also made of Toray FL96736-37K Type 40, Class 2, Style 6K-70-PW, Form 1 FRP material. The different peel plies were removed from both laminates just prior to bonding. Then AF 555 film adhesive was applied to either or both peel ply-treated surfaces.

It should be noted that the peel ply materials selected for use will depend on the particular FRP material that the test specimens are made of. For example, Toray FL96736-37K Type 40, Class 2, Style 6K-70-PW, Form 1 FRP is compatible with polyester peel ply (i.e., produces a surface suitable for bonding), while the Cytec CYCOM 950/PWC T300 FRP is not compatible with polyester peel ply.

Standards having a structure conforming to FIGS. 1 and 2 were assembled using this peel ply technology. Each standard was 18 inches long by 6 inches wide, resulting in a bonded joint having three zones (areas 12, 14 and 16 in FIG. 1) of 6×6 inches with respective different adhesive bond strengths.

The weak bond standards based on variable peel ply selection consisted of 16-ply graphite epoxy FRP material bonded to 20-ply graphite epoxy FRP material by a hot film bonding process using AF 555 adhesive with 350° F. curing. The three different types of peel ply identified in Table 1 (see Appendix) were used during the manufacturing process on one of the adherends. More specifically, three equal-size areas of one surface of the 16-ply graphite epoxy FRP material were respectively covered with the peel plies identified in Table 1 prior to curing of the FRP material. Similarly, an entire surface of the 20-ply graphite epoxy FRP material was covered with polyester peel ply BMS 8-308 prior to curing. After curing both FRP materials, the peel plies were removed, leaving consistent surface chemistry within each respective area of the 16-ply FRP laminate. AF 555 adhesive was then applied on one or both of the treated surfaces of the two FRP laminates and the laminates were pressed together with the adhesive therebetween. The adhesive was then cured at 350° F. The resulting bonded joint has three areas 12, 14 and 16 (see FIG. 1) with different adhesive bond strengths. In 2009 twelve standards were constructed and labeled WBPP1-CP1 through WBPP1-CP12.

Tables 2 and 3 (see Appendix) show the through transmission ultrasound (TTU) inspection scans of the twelve standards WBPP1-CP1 through WBPP1-CP12. The TTU signals do not indicate any differences between the respective peel ply regions. Tables 4 and 5 (see Appendix) are the pulse echo (PE) ultrasound inspection images of the same 12 standards. The PE results show bondline features due to the assembly, but no indications that identify a consistent change that could be correlated with the weak bond peel ply zones relative to the strong bond. The values shown are a ratio of the bondline signal to the front face signal. These data were taken from the 16-ply side of the samples. Similar images were obtained from the 20-ply side. The ultrasound inspection images showed no significant difference between the respective adhesive bond zones of the standards, providing no clue as to the strength in the various zones. Other NDI tests on the standards were also unable to distinguish a difference between the weak and strong bonded areas.

Weak Bond Standard Adhesive Strengths

Figure 3:
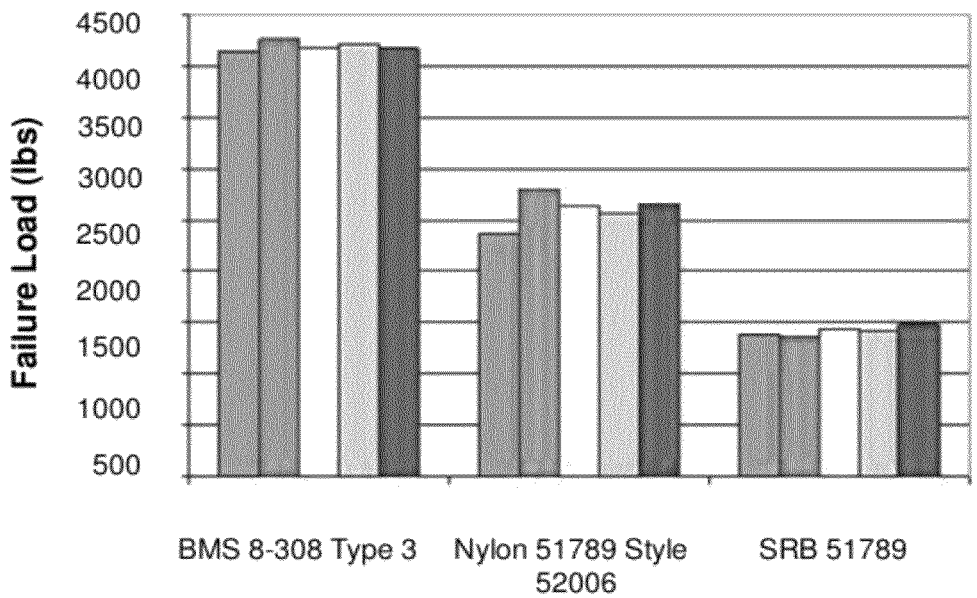
FIG. 3 is a bar chart showing lap shear failure loads for five weak bond test standards fabricated using the same set of three different peel ply materials.

The variable strength of the adhesive bonding using the peel ply surface preparation method from lap shear tests performed on five weak bond standards are shown in FIG. 3. Table 6 (see Appendix) summarizes the results of mechanical testing, i.e., lap shear, double cantilever beam (DCB) and flat-wise tension tests. The DCB and lap shear tests are baseline mechanical tests that demonstrate the success of the standard fabrication for creating variable adhesive bond strength. The lap shear tests were conducted in accordance with ASTM Standard D 3163-01; the Mode 1 interlaminar fracture toughness tests using DCB specimens were conducted in accordance with ASTM Standard D 5528-01. The flat-wise tension test was performed by using a trepanning method and bonding on an attachment. A tensile test load was applied by the DeFelsco adhesive bond tester. The trepanning flat-wise tension method involved drilling an annulus in one laminate to the bondline (leaving a center core of FRP material), fastening a plug to the center core of FRP material, and then applying tension on the plug until the center core of FRP material delaminated.

Weak Bond Standard Evaluation Methods

Nondestructive inspection has not been shown to be effective for finding weak bonds due to surface chemistry effects because there are no significant features to be detected at the interface. Nondestructive inspection operates in the elastic regime of materials, while strength is assessed in the plastic regime. Nondestructive inspection can detect weak bonds when the degradation of the bonds is due to feature changes that can be seen on NDI results. The weak bonds created by the peel ply method described above were shown to be undetectable by conventional ultrasonic NDI, which would be the standard inspection for a FRP-to-FRP bonded assembly.

Alternative methods that can be applied to bonds for testing are methods that stress the bond looking for deviation from standard response. Two methods tested were acoustic emission and laser bond inspection.

Figure 4:
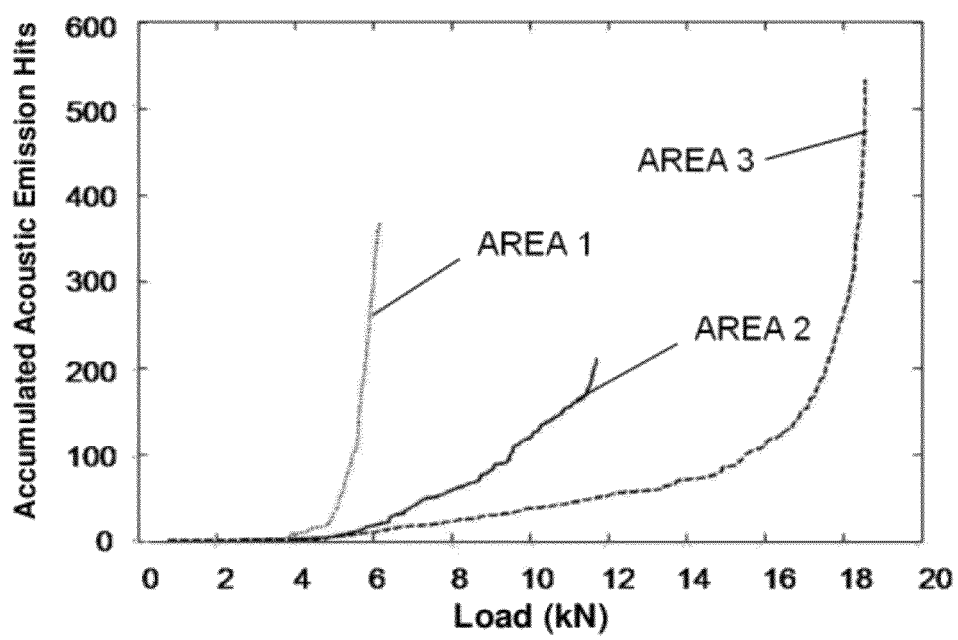
FIG. 4 is a graph showing accumulated acoustic emission hits versus load applied during lap shear testing for three areas of a weak bond test specimen assembly fabricated using three different peel ply materials.

The acoustic emission test was performed during lap shear testing. FIG. 4 shows the accumulated hits versus load (kN) for three adhesively bonded areas of a FRP test specimen assembly manufactured using peel plies as described above. Weaker bonds naturally create more hits as they approach failure. However for adequate testing, the loading would need to be relatively high, approaching 60% of the limit.

The laser bond inspection method uses high-intensity stress waves to create a tensile load at the bond interface. A detailed description of this method can be found in R. Bossi et al., "Laser Bonding Testing," *Materials Evaluation*, Vol. 67, No. 7, July 2009, pp. 819-827. Work was performed with the LBID system at LSP Technologies, Inc. in Dublin, Ohio. This system utilized a suitable Nd:glass laser (1054 nm wavelength). The laser produced 45 Joules/pulse with very high reproducibility. The laser was tailored to provide Gaussian-like pulse widths of 70 to 300 nsec.

Figure 5:
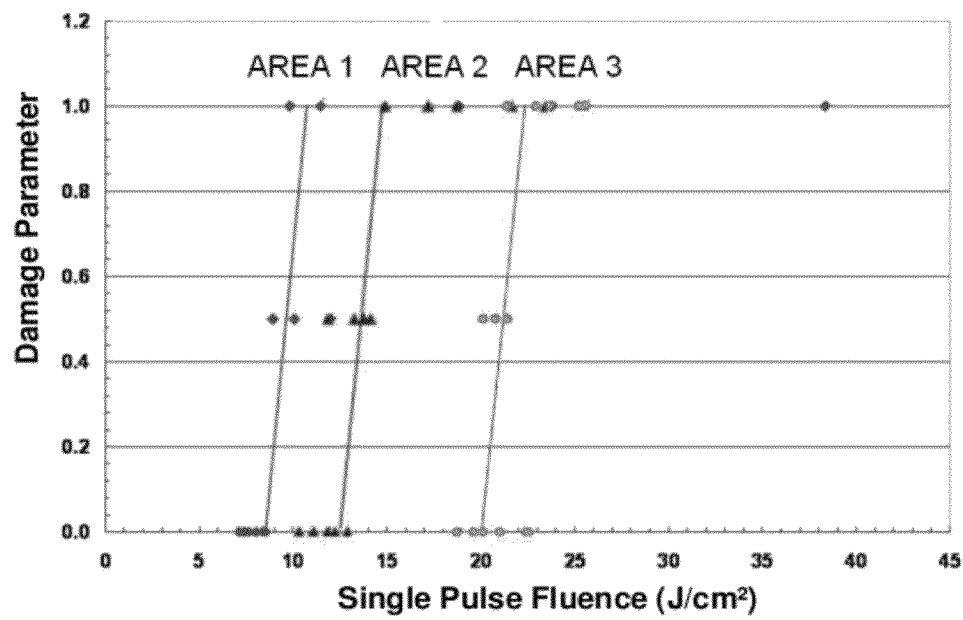
FIG. 5 is a plot of damage parameter versus laser fluence showing test results derived using a laser bond inspection method for three areas of a weak bond test specimen assembly fabricated using three different peel ply materials. The damage parameter varies from 0 (no damage) to 1 (debonded).

The weak peel ply bond standard was successfully tested using the laser bond inspection method. Table 7 (see Appendix) shows a summary of the laser bond inspection results. The relative power levels at which the SRB and nylon peel ply-treated surfaces fail relative to the polyester surface-treated baseline material are at 40% and 65% respectively. FIG. 5 shows a plot of the laser bond inspection test results over the three zones of the peel ply weak bond standard. The horizontal axis is the laser fluence. The vertical axis is a scale representing whether the bond failed or not, where 0 is no failure and 1 is clear failure. With increasing laser power, the weaker bond (Area 1) failed first; then the middle-strength bond (Area 2) failed; and then finally the full-strength bond (Area 3) failed. These data indicate that the laser bond inspection test is able to discriminate the weak bond standards fairly well.

Associated Peel Ply Weak Bond Creation

The weak bond standards described above were created using standard off-the-shelf peel ply material. These can be repeatably obtained and used for the construction. It is also possible to construct weak adhesion surfaces from peel ply material by modifying an existing peel ply material. In this case the peel ply material is allowed to soak in a solution of release agent material for a controlled time and then removed and dried. When differing concentrations or times are used for the bath, variable bond strengths may be obtained from the peel ply application in a bonding test.

In accordance with some embodiments, a commercially available peel ply material (e.g., a polyester peel ply material that had been scoured only and not heat set) can be soaked for a controlled time in a concentrated bath containing a release agent material (e.g., siloxane). By controlling the concentration and time, variable levels of peel ply contamination can be achieved. [The term "scouring" refers to an operation that is similar to a large washing machine that uses caustic chemicals. Its purpose is to remove any contaminants, such as oils and sizings, from all surfaces of the cloth. These contaminants may be put on the fabric to facilitate the previous weaving operations.]

In one study reported by P. Van Voast et al. in "Effect of Varying Levels of Peel Ply Contamination on Adhesion Threshold," SAMPE 2010, May 17-20, Seattle, Wash. (the contents of which are incorporated by reference herein in their entirety), polyester peel ply material was contaminated with mixes containing the following amounts of siloxane: 0% (deionized water), 0.0001%, 0.001%, 0.01%, 0.05%, 0.1%, 0.2%, 0.3%, 0.4%, 0.5%, 1% and 2%. The solutions were applied to fabric samples using a laboratory scale Werner Mathis AG textile padder and dried and heat set in a laboratory scale Werner Mathis AG tenter frame. The pressure at the pad was 400 kPa and the pad speed was 2.4 meters per minute. The contaminated samples were dried for 65 seconds at 188° C.

Figure 9:
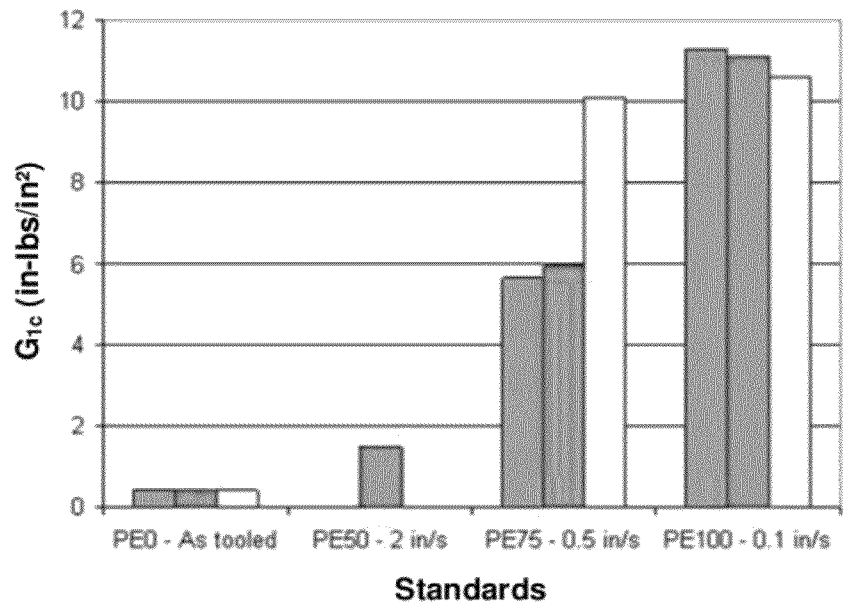

The FRP laminates used for this study were produced from 180° C. (350° F.) curing of carbon fiber-reinforced epoxy prepreg (Toray 3900-2/T800 Grade 190 tape). Polyester peel ply (Precision Fabric Group Style 60001) with a prescribed level of contamination was applied to the tool side of the laminate adherend. All laminate adherends were cured with a 2.8° C. (5° F.) per minute heat-up rate to 179° C. (355° F.) and allowed to dwell for 2 hours. The autoclave pressure was 0.58 MPa (85 psi) and full vacuum (29 mm Hg), which was maintained during the cure cycle. Bonding of the laminates was accomplished by removing the peel ply and applying one of four film adhesives. The adhesives evaluated were: 3M AF 555, Cytec Engineered Materials MB1515-3, Henkel EA9657 and PL795. Bond assemblies were cured with the same cure cycle as the laminates, except the pressure was reduced to 0.30 MPa (45 psi). Several adhesion tests were evaluated to determine their relative efficacy and adhesion threshold. Test results showed that the siloxane contamination had no measurable effect on adhesion until a threshold level of 1% siloxane contamination was reached. In particular, the DCB test results (see FIG. 9 in the Van Voast et al. article cited above) showed that the peel strength of the bonded assemblies decreased by at least 40% when the siloxane concentration was increased from 1% to 2%.

The calculated solids of siloxane is a more accurate method of discussing the level of contamination. The 2% contamination level corresponds to 4923 ppm siloxane in the mix. The levels of siloxane expected to be most useful for producing incremental weak bonds are in the range of 1000 to 6000 ppm calculated siloxane solids.

In order to manufacture test specimen assemblies using peel ply having varying levels of contamination, tests can be performed to find those contamination levels which produce in respective areas adhesive bond strengths reduced by respective percentages. For example, a test specimen assembly of the type depicted in FIG. 1 can be fabricated in which areas 12, 14 and 16, having respective different adhesive bond strengths, are produced using peel ply material having different levels of contamination. For example, the corresponding areas on the surface of a first FRP test specimen could be treated with peel ply material subjected to three different levels of contamination, while the surface of a second FRP test specimen (to be adhesively bonded to the first FRP test specimen to form a test specimen assembly) is treated with one peel ply material uniformly across all three areas. For example, the peel ply material having different levels of contamination can be produced by applying solutions containing different concentrations of siloxane.

Energetic Surface Preparations

Further embodiments of the invention rely on energetic surface preparation. The energetic surface preparation techniques disclosed below create a consistent bond that has controlled strength value based on the process. In addition, the zones of weakened strength in the test specimen assembly (i.e., bonded standard) may be of variable size and shape with no detectable physical edges. Further the variable strength is not detectable by features that can be detected by conventional NDI methods. The energetic method uses plasma or laser surface etching that is robotically controlled to produce variable surface conditions on FRP adherends. The robotic controller is a processor programmed for easy repetition and easy variation of the level of surface modification and of the shape of the treated zone. Bonds created by these methods will appear consistent over the entire standard by conventional NDI examinations.

The preferred energetic surface preparation techniques use either a plasma or laser etching process to modify the surface of a FRP adherend. These two processes are described in the next sections. The development of weak bond standards in the following discussion of energetic surface preparation discussion is for FRP-to-FRP joints.

Plasma Etch Surface Preparation

Plasma etching is a surface treatment method that uses gases in a plasma state of ions, electrons and excited species. The interaction of the plasma gas with the surface of a polymer will result in surface modification. The interaction occurs in the first few atomic layers, causing bonds to break and creating an energized surface. The bulk property of the polymer is not affected. The surface however is activated, increasing the wettability and improving bonding. Gases can be specific, such as noble gases, oxygen or nitrogen, but even air plasma is acceptable.

In accordance with one surface treatment method, a surface of a FRP substrate was exposed to a plasma jet generated by an atmospheric (i.e., open-air) plasma generator. The plasma generator used was Model FG1001 with a flume (rotation jet) head model No. RD1004 commercially available from Plasmatreat North America, Inc. This plasma generator was operated with the following parameters: Power—140 volts and 8.5-9.0 amperes; Air Pressure—45 psi; Flume Head Rotation—On. The plasma generator was mounted on a robotic arm. Robotic arm and platen model No. I&J2400 (industrial robot), commercially available from Fisnar Inc. Wayne, N.J., was used.

The atmospheric plasma generator uses compressed air to make a nitrogen-oxygen plasma. A vacuum chamber or shielded environment is not needed. Plasma units can use compressed air as the standard gas input, or can employ other gas inputs to achieve specific surface properties. The plasma oxidizes contaminants from the treated surface and can be used to alter the surface chemistry by reacting ions and free radicals in the plasma with that surface. The Plasmatreat Model FG1001 plasma generator with flume head model No. RD1004 produces a plasma flume that can be rotated to create a plasma ring.

The plasma flume was raster scanned over the FRP surface using the robotic arm. Variables that were controlled during the process included the flume head height, rastering speed and flume rotation. Head height is the distance from the tip of the flume head to the FRP surface. Rastering speed is how fast the flume head travels over the FRP surface. Flume rotation is specific to the flume jet used. The plasma flume can be used as a single jet or the flume can be rotated, creating a ring of plasma with a diameter of approximately 20 mm. This spreads the flume out so a larger surface area can be treated and lessens the effect of overlap when raster scanning in an x-y coordinate system. All tests were conducted with the flume rotation on and with a 50% overlap in the rastering pattern.

Figure 6:
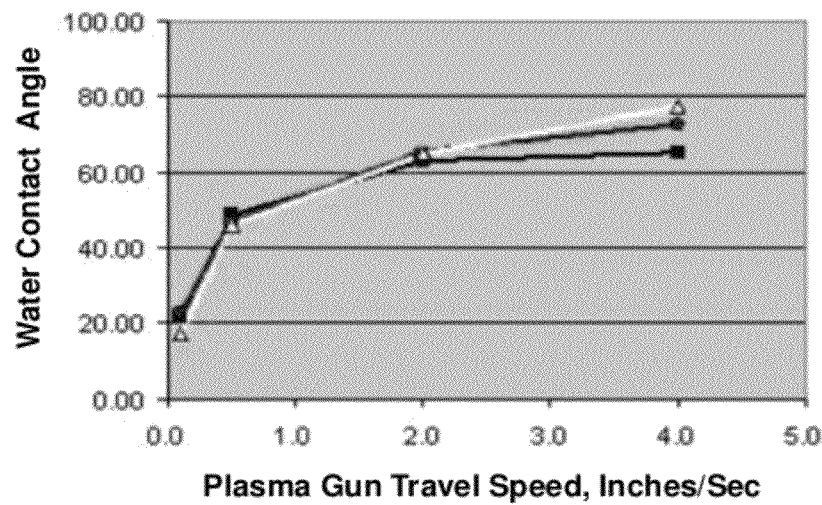
FIG. 6 is a plot showing water contact angle measurements at three time intervals after activation (■: 1 hr; ●: 5 hr; Δ: 24 hr) as a function of the travel speed (inches/sec) of a plasma gun following plasma treatment at a gun height of 0.50 inch.
Figure 7:
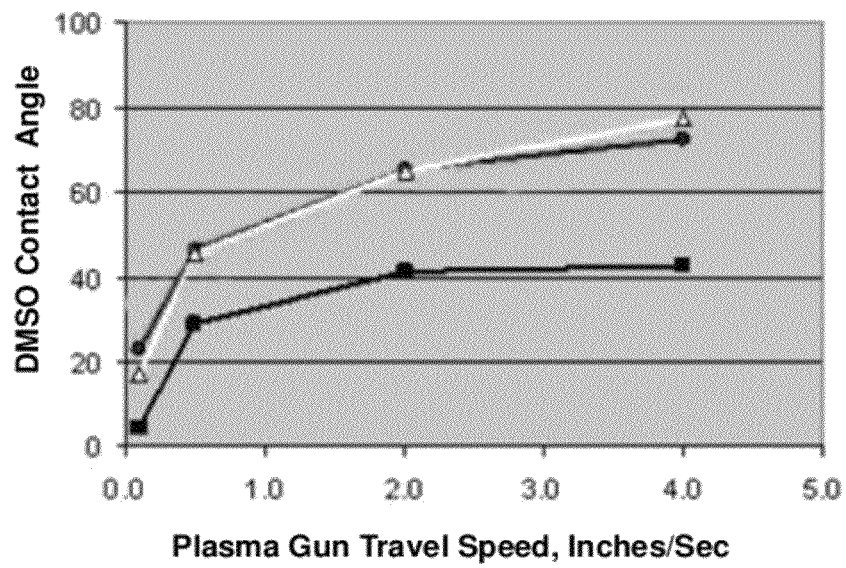
FIG. 7 is a plot showing DMSO contact angle measurements three time intervals after activation (■: 1 hr; ●: 5 hr; Δ: 24 hr) as a function of the travel speed (inches/sec) of a plasma gun following plasma treatment at a gun height of 0.50 inch.

To develop weak bond standards using plasma etching, a test was performed to measure the surface energy as a function of plasma etching parameters. FIGS. 6 and 7 respectively show the contact angle measurements for surface energy from water and dimethyl sulfoxide (DMSO) taken on the surface of a treated panel. The surface was FRP fabric of Toray FL96736-37K Type 40, Class 2, Style 6K-70-PW, Form 1. The graphs plot the contact angle versus the travel speed of the plasma treater. The head height to the surface was 0.5 inch. Other head heights were tested with 0.5 inch being selected based on the range of values in the contact angle curves. The results for DMSO contact angle show a shift of the surface energy between 1 and 5 hours that is not seen with the water contact angle. Based on these curves, significant changes in wettability should take place for plasma head travel speeds between 0.1 and 2 inches/sec when used at a 0.5-inch head height above the object.

Based on the curves seen in FIGS. 6 and 7, plasma etching was performed to create double cantilever beam (DCB) test standards for determining bond strength as a function of plasma etching level. The surfaces of both DCB adherends were plasma etched using the same process parameters. Table 8 (see Appendix) shows the plasma etch levels selected for the testing of respective DCB samples. The activity of the plasma on a surface is controlled by the energy of the plasma source, the distance from the surface, and the travel speed over the surface. For this test, the plasma energy and distance from the substrate were held constant and the travel speed was varied. The DCB samples were made with 13-ply laminates that consisted of a first ply of Toray FL96736-37K Type 40, Class 2, Style 6K-70-PW, Form 1 FRP fabric, eleven (0 degree orientation) plies of Toray P2352W-19 Type 35, Class 10, Grade 190, Form 3 tape and then a last ply of the same fabric. The plasma-etched laminates were bonded together using Henkel EA9696, Grade 10 250° F.-curing epoxy adhesive.

Following bonding the samples were inspected using Through Transmission Ultrasound (TTU) imaging of the post-cured samples. The TTU signal data in the bond region for the four samples were as follows: PE0—17.2±0.5 dB; PE50—17.3±0.9 dB; PE75—16.8±0.5 dB; PE100—16.9±0.5 dB. The data indicates that there were no significant differences between the samples with different levels of plasma etch surface preparation using a standard NDI technique.

Figure 8:
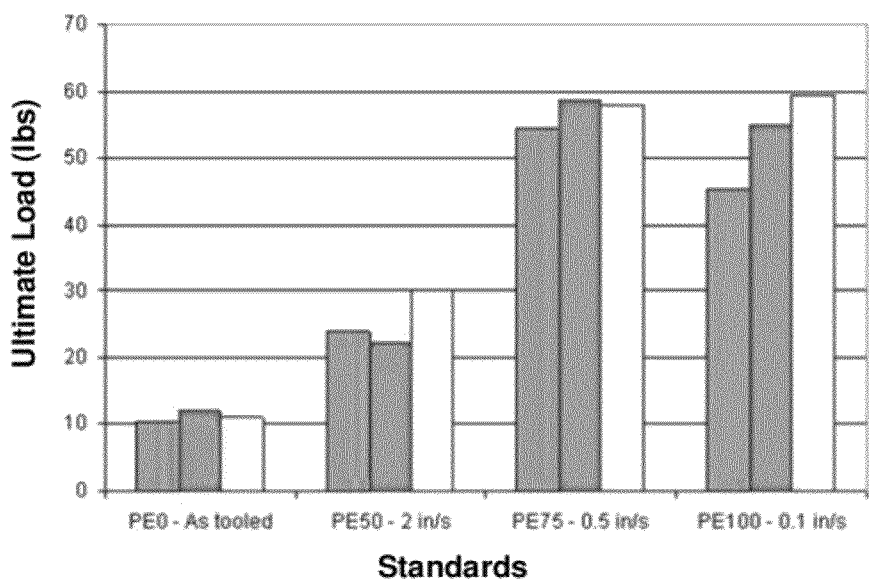
FIGS. 8 and 9 are respective bar charts showing ultimate loads and mode 1 crack strain energy release rates $G_{1c}$ for a plurality of test standards subjected to a double cantilever beam (DCB) test method, one set of three test standards being as tooled and the others having been treated by plasma etching at different plasma gun speeds.

Three DCB test standards were created from each bonded sample and testing was performed. The testing includes acoustic emission sensors. DCB testing measures the mode 1 crack strain energy release rate $G_{1c}$. The DCB ultimate load and $G_{1c}$ values are plotted in FIGS. 8 and 9 respectively. Table 9 (see Appendix) summarizes the values. In the case of the weak plasma etch (2 inches/sec), the $G_{1c}$ values could not be calculated accurately. A review of the surface failures indicated cohesive failure for the PE100, 0.1 inch/sec standards, a mixed cohesive interfacial failure for the PE75, 0.5 inch/sec standards and interfacial failure for the PE50, 2 inches/sec and PE0, as-tooled standards. Based on these tests, plasma etching can be a suitable source for creating controlled weak bonds in a FRP test specimen assembly.

In order to manufacture test specimen assemblies using plasma etching, tests can be performed to find those plasma etching parameters which respectively produce adhesive bond strengths reduced by respective percentages. For example, a test specimen assembly of the type depicted in FIG. 1 can be fabricated in which areas 12, 14 and 16, having respective different adhesive bond strengths, are produced using different plasma etching levels. For example, the corresponding areas on the surface of a first FRP test specimen could be subjected to three different plasma etching levels, while the surface of a second FRP test specimen (to be adhesively bonded to the first FRP test specimen to form a test specimen assembly) is subjected to uniform plasma etching across all three areas. The different plasma etching levels applied to the surface of the first FRP test specimen can be achieved by varying one or more of a plurality of plasma process parameters selected from the group comprising: travel speed of the plasma jet source, energy of the plasma jet source, and distance of the plasma jet source from the surface of the FRP test specimen.

Laser Etch Surface Preparation

Laser systems can be used to treat the surfaces of FRP substrates. The neodymium-doped yttrium aluminum garnet (Nd:YAG) laser is the most common laser in use and such lasers are commercially available in a variety of configurations and optical packages.

Laser surface preparation uses laser beam energy to affect the surface condition of the bond interface. The laser removes a thin film of resin from the FRP surface, leaving a pristine bonding surface similar to peel ply. It is highly dependent on the type of laser used and wavelength generated. The 1064 nm wavelength generated by most Nd:YAG lasers is absorbed by carbon fibers. This breaks apart the fiber and ablates the surface of the resin, leaving behind a weak crystalline structure unsuitable for bonding. Frequency doubling and tripling can be used to change the wavelength. An ideal treatment would utilize a wavelength that is absorbed by the resin and leaves the fibers undamaged. Factors such as power output of a pulsed laser beam source, pulse frequency of the pulsed laser beam, pulse repetition rate, diameter of the pulsed laser beam and step index of the laser beam spot can be varied depending on the laser system and optics chosen.

In a controlled study, laser processing was compared with the plasma etching and grit blasting methods. A frequency-tripled (1 watt) Nd:YAG laser was used to treat DCB adherends made of Toray FL96736-37K Type 40, Class 2, Style 6K-70-PW, Form 1 FRP material. The frequency-tripled wavelength of 355 nm is absorbed by the resin. The laser removed a thin film of resin, leaving behind a pristine bonding surface, similar to the effect of peel ply. It is also possible that there were changes in the surface chemistry of the resin. The laser was pulsed and the pulsed beam was raster scanned across the surface of the DCB adherends. The laser-etched DCB adherends were then bonded to form DCB specimens using EA9696 adhesive.

Figure 10:
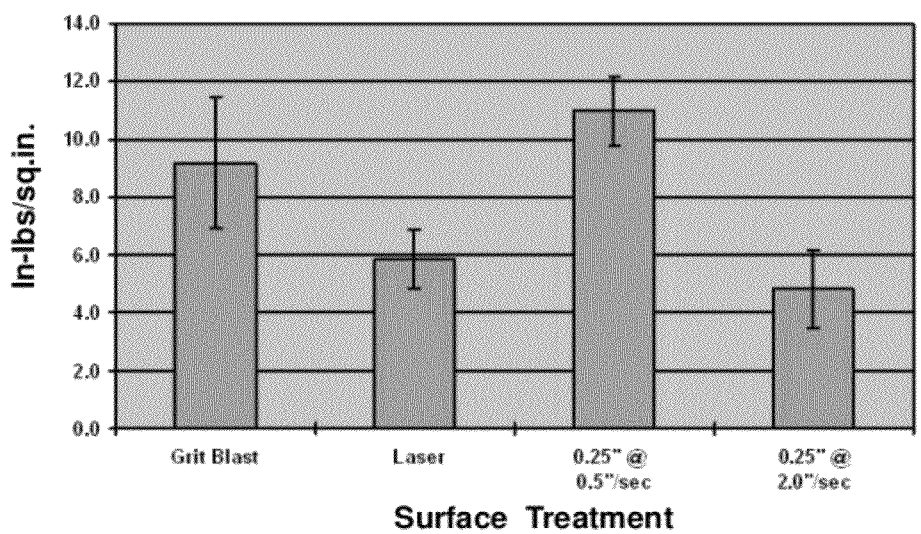
FIG. 10 is a bar chart showing mode 1 crack strain energy release rates $G_{1c}$ for a plurality of test standards subjected to a double cantilever beam (DCB) test method, the test standards being prepared using different surface preparation techniques, including grit blasting, laser etching and plasma etching at different travel speeds.

The DCB specimens prepared by laser etching were compared to specimens prepared by grit blasting and plasma etching. The $G_{IC}$ results are shown in Table 10 and FIG. 10. The laser preparation showed a weak bond that could similarly be obtained by grit blasting or plasma etching. Selection of variable laser power and dwell times could successfully create controlled weak bonds of variable strength.

In order to manufacture test specimen assemblies using laser etching, tests can be performed to find those laser etching parameters which respectively produce adhesive bond strengths reduced by respective percentages. For example, a test specimen assembly of the type depicted in FIG. 1 can be fabricated in which areas 12, 14 and 16, having respective different adhesive bond strengths, are produced using different laser etching levels. For example, the corresponding areas on the surface of a first FRP test specimen could be subjected to three different laser etching levels, while the surface of a second FRP test specimen (to be adhesively bonded to the first FRP test specimen to form a test specimen assembly) is subjected to uniform laser etching across all three areas. The different laser etching levels applied to the surface of the first FRP test specimen can be achieved by varying one or more of a plurality of laser process parameters selected from the group comprising: pulse frequency, power output, scanning speed and beam diameter.

Common Aspects of Disclosed Methods of Fabrication

The methods of fabricating test specimen assemblies disclosed above have the following aspects in common.

Figure 11:
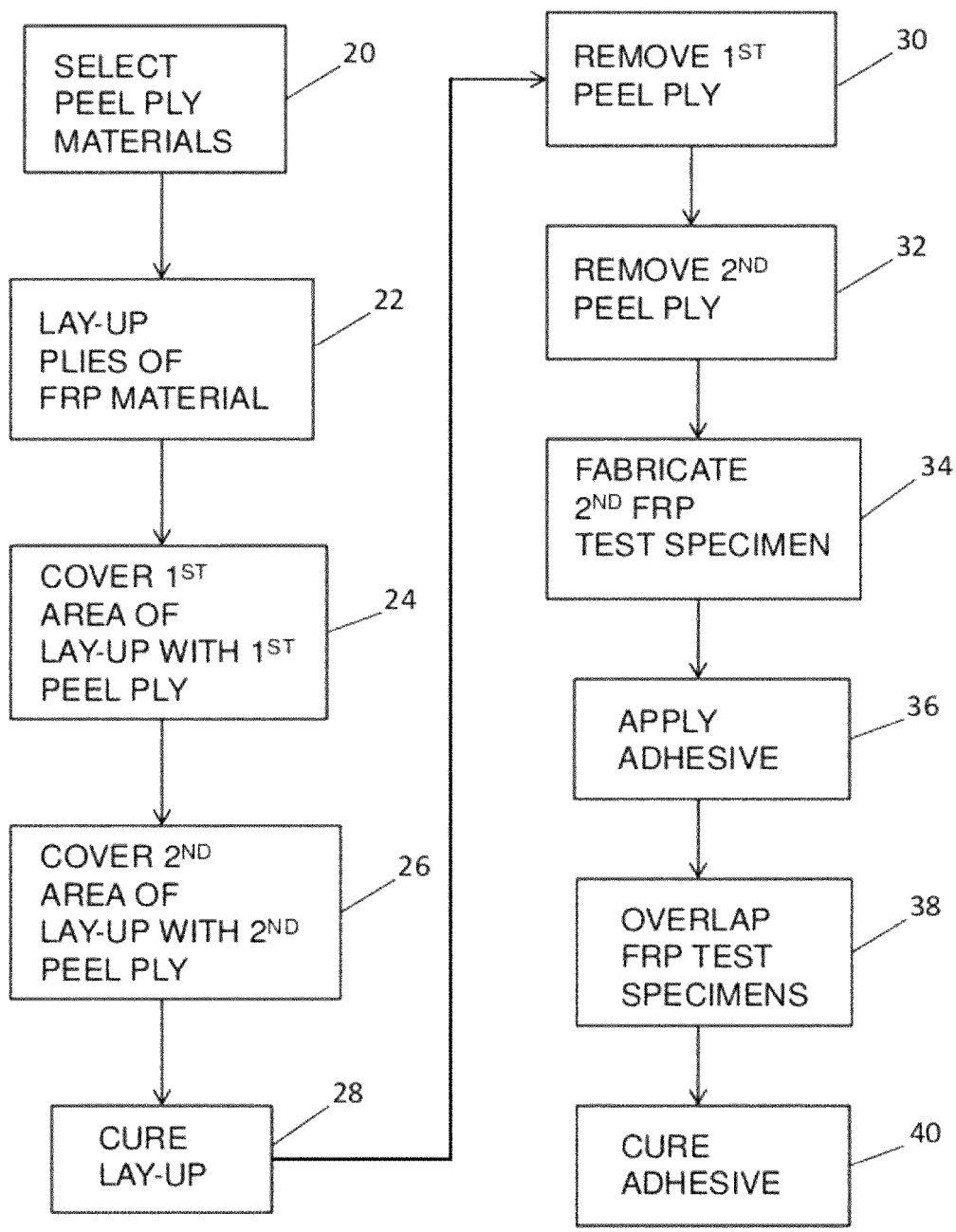
FIG. 11 is a flowchart showing common aspects of methods for repeatably fabricating a test specimen assembly having controlled variable bond strengths using peel ply material.

First, as shown in FIG. 11, each disclosed method for repeatably fabricating a test specimen assembly having controlled variable bond strengths using peel ply material comprises the following steps:

(a) selecting first and second peel ply materials, the first peel ply material being different than the second peel ply material (step 20 in FIG. 11);

(b) laying up a plurality of plies of fiber-reinforced plastic material (step 22);

(c) covering a first area of the lay-up with the first peel ply material (step 24);

(d) covering a second area of the lay-up with the second peel ply material, wherein the first and second areas do not overlap (step 26);

(e) curing the lay-up of fiber-reinforced plastic material with the first and second peel ply materials in place to form a first fiber-reinforced plastic test specimen (step 28);

(f) removing the first peel ply material to expose a first area of a bonding surface of the first fiber-reinforced plastic test specimen (step 30), the result being that the first area of the bonding surface of the first fiber-reinforced plastic test specimen has a first bonded joint performance-governing characteristic;

(g) removing the second peel ply material to expose a second area of the bonding surface of the first fiber-reinforced plastic test specimen (step 32), the result being that the second area of the bonding surface of the first fiber-reinforced plastic test specimen has a second bonded joint performance-governing characteristic different than the first bonded joint performance-governing characteristic;

(h) fabricating a second fiber-reinforced plastic test specimen having a bonding surface (step 34);

(i) applying adhesive on the bonding surface of one or both of the first and second fiber-reinforced plastic test specimens (step 36);

(j) placing the bonding surface of the first fiber-reinforced plastic test specimen in overlapping relationship with the bonding surface of the second fiber-reinforced plastic test specimen with the adhesive therebetween, the adhesive being in contact with the first and second areas of the bonding surface of the first fiber-reinforced plastic test specimen and with the bonding surface of the second fiber-reinforced plastic test specimen (step 38); and (i) curing the adhesive to bond the first and second fiber-reinforced plastic test specimens together (step 40).

Figure 12:
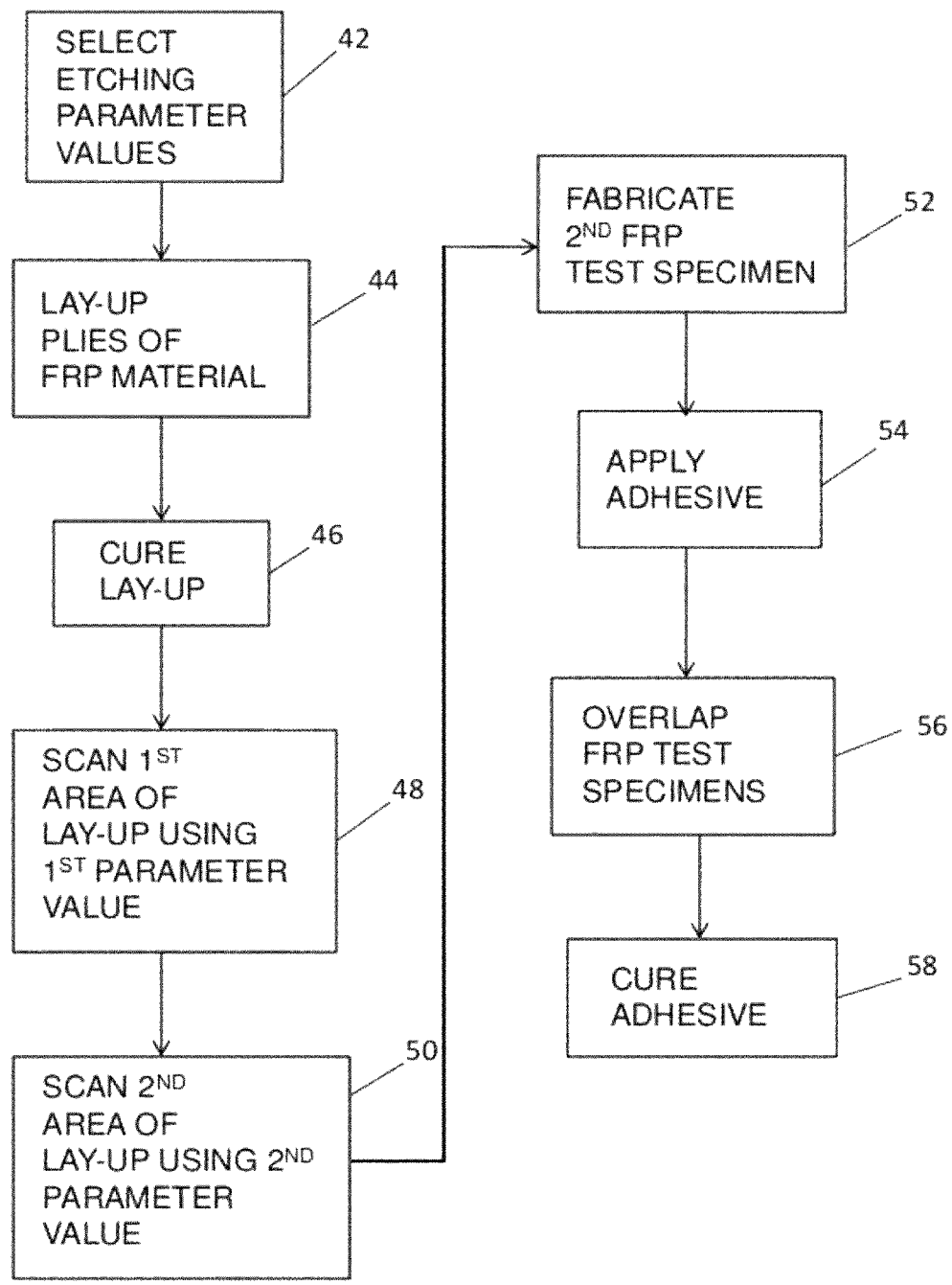
FIG. 12 is a flowchart showing common aspects of methods for repeatably fabricating a test specimen assembly having controlled variable bond strengths using plasma or laser etching.

Second, as shown in FIG. 12, each disclosed method for repeatably fabricating a test specimen assembly having controlled variable bond strengths using an etching process (i.e., plasma or laser) comprises the following steps:

(a) selecting first and second values of an etching process parameter, the first value being different than the second value (step 42 in FIG. 12);

(b) laying up a plurality of plies of fiber-reinforced plastic material (step 44);

(c) curing the lay-up of fiber-reinforced plastic material to form a first fiber-reinforced plastic test specimen having a bonding surface (step 46);

(d) moving a plasma jet or laser beam to scan over a first area of the bonding surface of the first fiber-reinforced plastic test specimen while the etching process parameter equals the first value (step 48), the result being that the first area of the bonding surface of the first fiber-reinforced plastic test specimen has a first bonded joint performance-governing characteristic;

(e) moving a plasma jet or laser beam to scan over a second area of the bonding surface of the first fiber-reinforced plastic test specimen while the etching process parameter equals the second value, wherein the first and second areas do not overlap (step 50), the result being that the second area of the bonding surface of the first fiber-reinforced plastic test specimen has a second bonded joint performance-governing characteristic different than the first bonded joint performance-governing characteristic;

(f) fabricating a second fiber-reinforced plastic test specimen having a bonding surface (step 52);

(g) applying adhesive on the bonding surface of one or both of the first and second fiber-reinforced plastic test specimens (step 54);

(h) placing the bonding surface of the first fiber-reinforced plastic test specimen in overlapping relationship with the bonding surface of the second fiber-reinforced plastic test specimen with the adhesive therebetween, the adhesive being in contact with the first and second areas of the bonding surface of the first fiber-reinforced plastic test specimen and with the bonding surface of the second fiber-reinforced plastic test specimen (step 56); and (i) curing the adhesive to bond the first and second fiber-reinforced plastic test specimens together (step 58).

Figure 13:
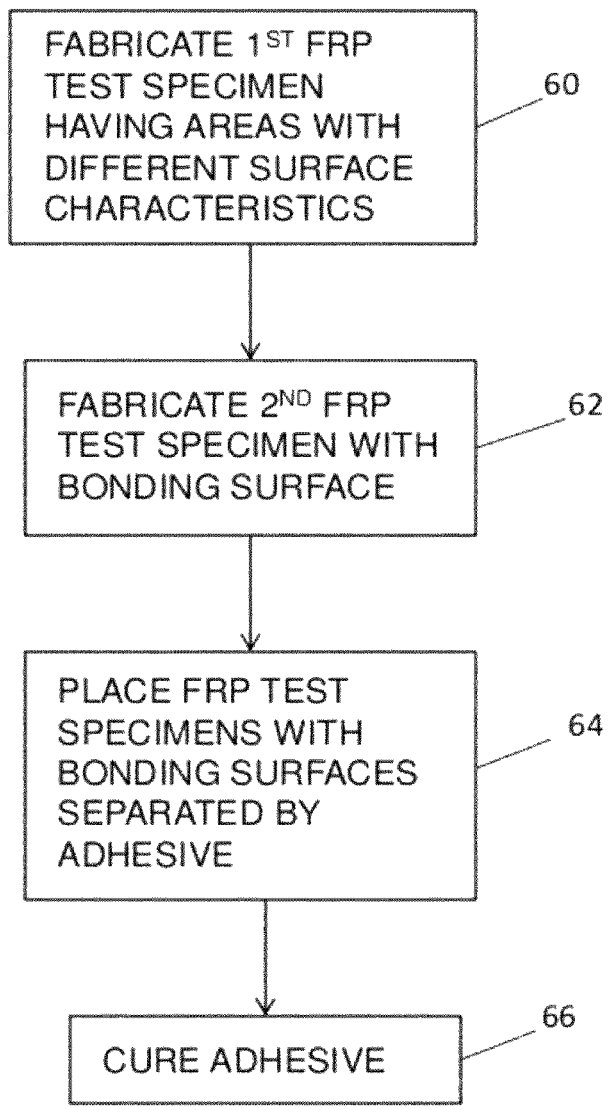
FIG. 13 is a flowchart showing common aspects of the fabrication methods depicted in FIGS. 11 and 12.

Moreover, as shown in FIG. 13, the common aspects of the fabrication methods depicted in FIGS. 11 and 12 comprise the following steps:

(a) fabricating a first fiber-reinforced plastic test specimen having a bonding surface, wherein a first area of the bonding surface of the first fiber-reinforced plastic test specimen has a first bonded joint performance-governing characteristic, while a second area of the bonding surface, not overlapping with the first area, of the first fiber-reinforced plastic test specimen has a second bonded joint performance-governing characteristic different than the first bonded joint performance-governing characteristic (step 60 in FIG. 13);

(b) fabricating a second fiber-reinforced plastic test specimen having a bonding surface (step 62);

(c) placing the bonding surface of the first fiber-reinforced plastic test specimen in overlapping relationship with the bonding surface of the second fiber-reinforced plastic test specimen with adhesive therebetween, the adhesive being in contact with the first and second areas of the bonding surface of the first fiber-reinforced plastic test specimen and with the bonding surface of the second fiber-reinforced plastic test specimen (step 64); and (d) curing the adhesive to bond the first and second fiber-reinforced plastic test specimens together (step 66).

Figure 14:
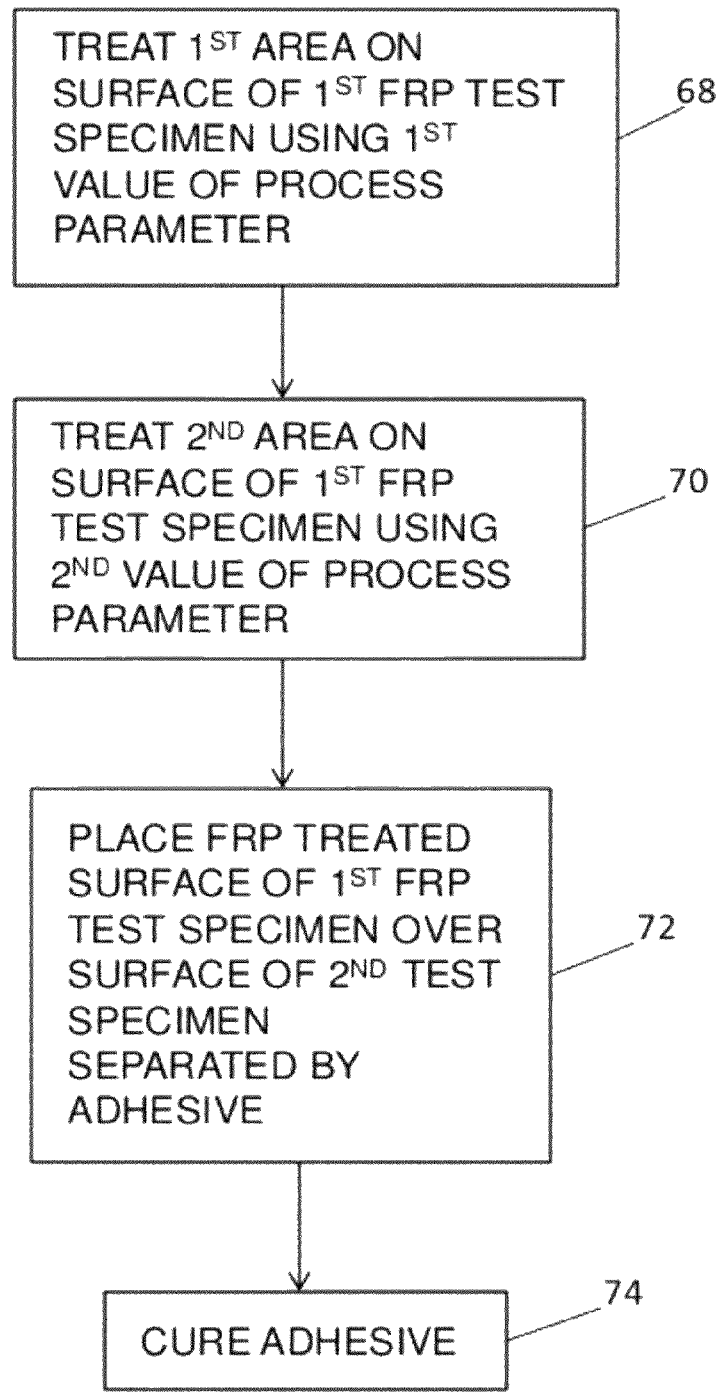
FIG. 14 is a flowchart showing the common aspects of the fabrication methods using plasma or laser etching wherein the common aspects are characterized more broadly than is done in FIG. 12.

Alternatively, as shown in FIG. 14, the common aspects of the above-disclosed fabrication methods using plasma or laser etching can be characterized more broadly as comprising the following steps:

(a) applying a first surface treatment process over a first area of a surface of a first fiber-reinforced plastic test specimen (step 68 in FIG. 14);

(b) applying a second surface treatment process over a second area of the surface of the first fiber-reinforced plastic test specimen, wherein each of the first and second surface treatment processes comprises a process parameter, the process parameter for the first surface treatment process being equal to a first value, and the process parameter for the second surface treatment process being equal to a second value that is different than the first value (step 70);

(c) placing the treated surface of the first fiber-reinforced plastic test specimen in overlapping relationship with a surface of a second fiber-reinforced plastic test specimen with adhesive therebetween, the adhesive being in contact with the first and second areas of the treated surface of the first fiber-reinforced plastic test specimen and with the surface of the second fiber-reinforced plastic test specimen (step 72); and (d) curing the adhesive to bond the first and second fiber-reinforced plastic test specimens together (step 74).

Utility of Disclosed Standards

Standards made using the techniques disclosed herein can be used as part of the certification of bonded structure where a validation of strength is required and a method of testing is used. When the bond strengths of these standards are measured, the results can demonstrate that the bond strength measurement technique used is sensitive to variations in bond strength and in calibration. The standards disclosed herein can be used to satisfy the FAA and DOD certification agencies that bonded structures are in fact strong because they provide a standard method to calibrate the methods for testing the bonds. The standards will be used in conjunction with the bonding assembly of FRP parts and the method of bond strength validation. The bond strength validation method will be tested on the standards prior to and after testing on the bonded assembly.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiments for carrying out this invention disclosed hereinabove.

The method claims set forth hereinafter should not be construed to require that the recited steps be performed in the order recited.

APPENDIX

TABLE 1

| Type | Comment |
|---|---|
| Nylon 6,6 SRB (Super Release Blue) (Precision Fabrics 51789 FIN 061) | Nylon-based peel ply with inert, heat-stabilized crosslinked polymer finish (siloxane) |
| Nylon 6,6 (Precision Fabrics 51789) | Nylon-based peel ply fabric |
| Polyester peel ply BMS 8-308 (Precision Fabrics 60001) | Polyester-based peel ply fabric |

TABLE 2

| Peel Ply Type | WBPP1-CP1 | WBPP1-CP2 | WBPP1-CP3 | WBPP1-CP4 | WBPP1-CP5 | WBPP1-CP6 |
|---|---|---|---|---|---|---|
| Polyester 600010 | 19.39 ± 1.02 | 19.54 ± 0.92 | 18.95 ± 0.68 | 19.14 ± 0.63 | 19.33 ± 0.64 | 19.27 ± 0.66 |
| Nylon 51789 | 19.88 ± 1.34 | 19.02 ± 0.67 | 19.08 ± 0.80 | 19.31 ± 0.73 | 19.01 ± 0.51 | 19.26 ± 0.58 |
| SRB 51789 | 20.11 ± 1.60 | 19.57 ± 0.88 | 18.91 ± 0.75 | 19.19 ± 0.55 | 19.16 ± 0.53 | 19.31 ± 0.60 |

TABLE 3

| Peel Ply Type | WBPP1-CP7 | WBPP1-CP8 | WBPP1-CP9 | WBPP1-CP10 | WBPP1-CP11 | WBPP1-CP12 |
|---|---|---|---|---|---|---|
| Polyester 600010 | 19.47 ± 0.75 | 19.39 ± 0.74 | 19.36 ± 0.84 | 19.47 ± 0.65 | 19.54 ± 0.60 | 19.54 ± 0.77 |
| Nylon 51789 | 19.53 ± 1.00 | 19.66 ± 1.24 | 19.23 ± 1.32 | 19.16 ± 0.77 | 19.35 ± 0.88 | 19.34 ± 0.63 |
| SRB 51789 | 19.27 ± 1.22 | 19.31 ± 1.49 | 19.15 ± 1.20 | 18.97 ± 1.03 | 19.33 ± 1.03 | 19.11 ± 0.78 |

TABLE 4

| Peel Ply Type | WBPP1-CP1 | WBPP1-CP2 | WBPP1-CP3 | WBPP1-CP4 | WBPP1-CP5 | WBPP1-CP6 |
|---|---|---|---|---|---|---|
| Polyester 600010 | 0.542 ± 0.046 | 0.563 ± 0.047 | 0.550 ± 0.043 | 0.551 ± 0.039 | 0.546 ± 0.039 | 0.557 ± 0.039 |
| Nylon 51789 | 0.547 ± 0.060 | 0.563 ± 0.049 | 0.550 ± 0.042 | 0.554 ± 0.045 | 0.541 ± 0.037 | 0.550 ± 0.042 |
| SRB 51789 | 0.566 ± 0.073 | 0.596 ± 0.052 | 0.520 ± 0.045 | 0.581 ± 0.049 | 0.555 ± 0.051 | 0.573 ± 0.048 |

TABLE 5

| Peel Ply Type | WBPP1-CP7 | WBPP1-CP8 | WBPP1-CP9 | WBPP1-CP10 | WBPP1-CP11 | WBPP1-CP12 |
|---|---|---|---|---|---|---|
| Polyester 600010 | 0.566 ± 0.042 | 0.562 ± 0.033 | 0.554 ± 0.044 | 0.543 ± 0.044 | 0.559 ± 0.038 | 0.529 ± 0.039 |
| Nylon 51789 | 0.568 ± 0.050 | 0.565 ± 0.062 | 0.558 ± 0.039 | 0.534 ± 0.047 | 0.541 ± 0.034 | 0.509 ± 0.039 |
| SRB 51789 | 0.593 ± 0.044 | 0.590 ± 0.051 | 0.566 ± 0.043 | 0.546 ± 0.046 | 0.557 ± 0.038 | 0.537 ± 0.038 |

TABLE 6

| Peel ply | DCB Relative $G_{1c}$ | Relative Lap Shear | Relative Trepanned Tensile Test |
|---|---|---|---|
| BMS 8-308 | 100 | 100 | 100 |
| Nylon | 14 | 62 | 80 |
| SRB | 7 | 33 | 64 |

TABLE 7

| Peel Ply Zone | Relative LBID Failure Power Level | Relative Lap Shear Strength | Relative DCB Ultimate Strength | Relative DCB $G_{1c}$ |
|---|---|---|---|---|
| SRB | 40 | 33 | 18 | 7 |
| Nylon | 65 | 62 | 32 | 14 |
| Polyester 600010 | 100 | 100 | 100 | 100 |

TABLE 8

| | Plasma Etch Level | |
|---|---|---|
| Sample Label | Plasma Gun Height | Plasma Gun Speed |
| PE0 | NA - as tooled surface | NA - as tooled surface |
| PE50 | 0.5 inch | 2 inches/second |
| PE75 | 0.5 inch | 0.5 inches/second |
| PE100 | 0.5 inch | 0.1 inches/second |

TABLE 9

| Sample | $G_{1c}$ (inch-lbs/inch$^2$) | Ultimate Load (lbs) |
|---|---|---|
| PE0 - As tooled | 0.43 ± 0.02 | 11.1 ± 0.9 |
| PE50 - 2 inches/sec | 1.5 (one sample) | 25.4 ± 4 |
| PE75 - 0.5 inch/sec | 7.2 ± 2.5 | 57 ± 07 |
| PE100 - 0.1 inch/sec | 11 ± 0.4 | 53 ± 7 |

TABLE 10

| | Individual $G_{Ic}$ Values (lb/in$^2$) | | | | | | |
|---|---|---|---|---|---|---|---|
| Surface Preparation | 1 | 2 | 3 | 4 | 5 | Avg. | St.Dev. |
| Grit Blasting | 5.52 | 8.90 | 11.00 | 11.09 | 9.32 | 9.17 | 1.26 |
| Laser Etching | 4.23 | 6.26 | 6.74 | 6.55 | 5.60 | 5.88 | 1.02 |
| Plasma Etching 0.25" @ 0.5"/sec | 8.90 | 11.12 | 11.36 | 11.88 | 11.67 | 10.98 | 1.20 |
| Plasma Etching 0.25" @ 2.0"/sec | 2.60 | 4.67 | 4.95 | 6.04 | 5.82 | 4.81 | 1.38 |

The invention claimed is:

1. A method for repeatably fabricating a test specimen assembly having controlled variable bond strengths, comprising the following steps:
   (a) fabricating a first fiber-reinforced plastic test specimen having a bonding surface, wherein a first area of said bonding surface of said first fiber-reinforced plastic test specimen has a first bonded joint performance-governing characteristic, while a second area of said bonding surface, not overlapping with said first area, of said first fiber-reinforced plastic test specimen has a second bonded joint performance-governing characteristic different than said first bonded joint performance-governing characteristic;
   (b) fabricating a second fiber-reinforced plastic test specimen having a bonding surface;
   (c) placing said bonding surface of said first fiber-reinforced plastic test specimen in overlapping relationship with said bonding surface of said second fiber-reinforced plastic test specimen with adhesive therebetween, the adhesive being in contact with said first and second areas of said bonding surface of said first fiber-reinforced plastic test specimen and with said bonding surface of said second fiber-reinforced plastic test specimen; and
   (d) curing the adhesive to bond said first and second fiber-reinforced plastic test specimens together.

2. The method as recited in claim 1, further comprising the step of selecting first and second values of a plasma process parameter, said first value being different than said second value, wherein step (a) comprises the following steps performed in the order listed:
   laying up a plurality of plies of fiber-reinforced plastic material;
   curing said lay-up of fiber-reinforced plastic material;
   moving a plasma jet to scan over said first area while said plasma process parameter equals said first value; and
   moving a plasma jet to scan over said second area while said plasma process parameter equals said second value.

3. The method as recited in claim 2, wherein said plasma process parameter is selected from the group comprising: travel speed of a plasma jet source, energy of a plasma jet source, and distance of a plasma jet source from said surface of said first fiber-reinforced plastic test specimen.

4. The method as recited in claim 1, further comprising the step of selecting first and second values of a laser process parameter, said first value being different than said second value, wherein step (a) comprises the following steps performed in the order listed:
   laying up a plurality of plies of fiber-reinforced plastic material;
   curing said lay-up of fiber-reinforced plastic material;
   moving a laser beam to scan over said first area while said laser process parameter equals said first value; and
   moving a laser beam to scan over said second area while said laser process parameter equals said second value.

5. The method as recited in claim 4, wherein said laser process parameter is selected from the group comprising: power output of a pulsed laser beam source, pulse frequency of said pulsed laser beam, pulse repetition rate, diameter of said pulsed laser beam and step index of the laser beam spot.

6. The method as recited in claim 1, further comprising the step of selecting first and second peel ply materials, said first peel ply material being different than said second peel ply material, wherein step (a) comprises the following steps:
   laying up a plurality of plies of fiber-reinforced plastic material;
   covering said lay-up with said first peel ply material in said first area;

covering said lay-up with said second peel ply material in said second area;
curing said lay-up of fiber-reinforced plastic material;
removing said first peel ply material; and
removing said second peel ply material.

7. The method as recited in claim 6, wherein said first peel-ply material comprises filaments made of a first polymeric material and said second peel-ply material comprises filaments made of a second polymeric material different than said first polymeric material.

8. The method as recited in claim 6, wherein said first and second peel ply materials comprise filaments made of a polymeric material, further comprising the step of soaking at least one of said first and second peel ply materials in a solution of a release agent.

9. The method as recited in claim 6, wherein one of said first and second peel ply materials has an inert, heat-stabilized cross-linked polymer finish and the other does not.

10. The method as recited in claim 6, wherein said first and second peel ply materials comprise filaments made of a polymeric material, further comprising the steps of soaking said first peel ply material in a solution of a release agent having a first concentration for a first soaking time, and soaking said second peel ply material in a solution of said release agent having a second concentration for a second soaking time, wherein said first and second concentrations and said first and second soaking times are selected to achieve different levels of contamination by said release agent in said first and second peel ply materials.

11. A test specimen assembly fabricated by a process comprising the following steps:
(a) fabricating a first fiber-reinforced plastic test specimen having a bonding surface, wherein a first area of said bonding surface of said first fiber-reinforced plastic test specimen has a first bonded joint performance-governing characteristic, while a second area of said bonding surface, not overlapping with said first area, of said first fiber-reinforced plastic test specimen has a second bonded joint performance-governing characteristic different than said first bonded joint performance-governing characteristic;
(b) fabricating a second fiber-reinforced plastic test specimen having a bonding surface;
(c) placing said bonding surface of said first fiber-reinforced plastic test specimen in overlapping relationship with said bonding surface of said second fiber-reinforced plastic test specimen with adhesive therebetween, the adhesive being in contact with said first and second areas of said bonding surface of said first fiber-reinforced plastic test specimen and with said bonding surface of said second fiber-reinforced plastic test specimen; and
(d) curing the adhesive to bond said first and second fiber-reinforced plastic test specimens together.

12. The test specimen assembly as recited in claim 11, wherein the adhesive bond in said first area has a first adhesive bond strength and the adhesive bond in said second area has a second adhesive bond strength that differs from said first adhesive bond strength, wherein said difference between said first and second adhesive bond strengths is detectable by a destructive testing technique, but is not detectable via ultrasonic nondestructive inspection techniques.

13. A fiber-reinforced plastic test standard comprising first and second fiber-reinforced plastic laminates having opposing surfaces bonded by cured adhesive, the opposing surface of said first fiber-reinforced plastic laminate having a first area with a first set of surface characteristics and a second area with a second set of surface characteristics different than said first set of surface characteristics, the opposing surface of said second fiber-reinforced plastic laminate having first and second areas with uniform surface characteristics, and the first and second areas of the surface of said first fiber-reinforced plastic laminate respectively confronting the first and second areas of the surface of said second fiber-reinforced plastic laminate, the cured adhesive between said first areas forming a first adhesive bond having a first adhesive bond strength and the cured adhesive between said second areas forming a second adhesive bond having a second adhesive bond strength which is different than said first adhesive bond strength.

14. The standard as recited in claim 13, wherein the difference between said first and second adhesive bond strengths is detectable by a destructive testing technique, but is not detectable via ultrasonic nondestructive inspection techniques.

15. The standard as recited in claim 13, wherein said first adhesive bond strength is less than said second adhesive bond strength by at least 25% of said second adhesive bond strength.

16. A method for fabricating a test specimen assembly, comprising the following steps:
(a) applying a first surface treatment process over a first area of a surface of a first fiber-reinforced plastic test specimen;
(b) applying a second surface treatment process over a second area of said surface of said first fiber-reinforced plastic test specimen, wherein each of said first and second surface treatment processes comprises a process parameter, said process parameter for said first surface treatment process being equal to a first value, and said process parameter for said second surface treatment process being equal to a second value that is different than said first value;
(c) placing said treated surface of said first fiber-reinforced plastic test specimen in overlapping relationship with a surface of a second fiber-reinforced plastic test specimen with adhesive therebetween, the adhesive being in contact with said first and second areas of said treated surface of said first fiber-reinforced plastic test specimen and with said surface of said second fiber-reinforced plastic test specimen; and
(d) curing the adhesive to bond said first and second fiber-reinforced plastic test specimens together.

17. The method as recited in claim 16, wherein said process parameter is a plasma process parameter, said first surface treatment process comprises moving a plasma jet to scan over said first area of said surface of said first fiber-reinforced plastic test specimen while said plasma process parameter equals said first value, and said second surface treatment process comprises moving a plasma jet to scan over said second area of said surface of said first fiber-reinforced plastic test specimen while said plasma process parameter equals said second value.

18. The method as recited in claim 17, wherein said plasma process parameter is selected from the group comprising: travel speed of a plasma jet source, energy of a plasma jet source, and distance of a plasma jet source from said surface of said first fiber-reinforced plastic test specimen.

19. The method as recited in claim 16, wherein said process parameter is a laser process parameter, said first surface treatment process comprises moving a laser beam to scan over said first area of said surface of said first fiber-reinforced plastic test specimen while said laser process parameter equals said first value, and said second surface treatment process comprises moving a laser beam to scan over said second area of said surface of said first fiber-reinforced plastic test specimen while said laser process parameter equals said second value.

20. The method as recited in claim 19, wherein said laser process parameter is selected from the group comprising: power output of a pulsed laser beam source, pulse frequency of said pulsed laser beam, pulse repetition rate, diameter of said pulsed laser beam and step index of the laser beam spot.

* * * * *